United States Patent
Mass et al.

(10) Patent No.: US 6,889,086 B2
(45) Date of Patent: May 3, 2005

(54) PASSIVE TELEMETRY SYSTEM FOR IMPLANTABLE MEDICAL DEVICE

(75) Inventors: William R. Mass, Maple Grove, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/828,460

(22) Filed: Apr. 6, 2001

(65) Prior Publication Data

US 2002/0147388 A1 Oct. 10, 2002

(51) Int. Cl.$^7$ .............................................. A61N 1/02
(52) U.S. Cl. ...................................... 607/60; 128/903
(58) Field of Search .......................... 607/30, 32, 60; 123/903

(56) References Cited

U.S. PATENT DOCUMENTS

| | | | |
|---|---|---|---|
| 3,218,638 A | 11/1965 | Honig | 342/50 |
| 3,897,753 A | 8/1975 | Lee et al. | 119/51 R |
| 3,964,024 A | 6/1976 | Hutton et al. | 340/152 T |
| 4,019,179 A | 4/1977 | Sivertson, Jr. | 343/5 MM |
| 4,075,632 A * | 2/1978 | Baldwin et al. | 342/51 |
| 4,129,855 A | 12/1978 | Rodrian | 340/152 T |
| 4,262,632 A | 4/1981 | Hanton et al. | 119/1 |
| 4,494,545 A * | 1/1985 | Slocum et al. | 607/32 |
| 4,510,495 A | 4/1985 | Sigrimis et al. | 340/825.54 |
| 4,532,932 A * | 8/1985 | Batty, Jr. | 607/32 |
| 4,565,980 A | 1/1986 | Ashida | 332/105 |
| 4,681,111 A * | 7/1987 | Silvian | |
| 5,137,022 A | 8/1992 | Henry | 128/419 PT |
| 5,254,997 A | 10/1993 | Cohn | 342/44 |
| 5,260,701 A * | 11/1993 | Guern et al. | 340/10.34 |
| 5,314,457 A * | 5/1994 | Jeutter et al. | |
| 5,466,246 A * | 11/1995 | Silvian | 607/32 |
| 5,517,194 A | 5/1996 | Carroll et al. | 342/50 |
| 5,562,713 A | 10/1996 | Silvian | 607/32 |
| 5,683,432 A | 11/1997 | Goedeke et al. | 607/32 |
| 5,787,174 A | 7/1998 | Tuttle | 380/23 |
| 5,999,857 A * | 12/1999 | Weijand et al. | 128/903 |
| 6,100,840 A | 8/2000 | Zidek et al. | 342/42 |
| 6,104,311 A | 8/2000 | Lastinger | 340/825.54 |
| 6,108,367 A | 8/2000 | Herman et al. | 375/141 |
| 6,154,136 A | 11/2000 | Van Eeden | 340/572.1 |
| 6,201,993 B1 | 3/2001 | Kruse et al. | 607/32 |
| 6,236,889 B1 * | 5/2001 | Soykan et al. | 607/30 |
| 6,243,013 B1 | 6/2001 | Duan et al. | 340/572.7 |
| 6,301,504 B1 * | 10/2001 | Silvian | 607/60 |
| 2002/0151770 A1 * | 10/2002 | Noll et al. | 600/300 |

* cited by examiner

*Primary Examiner*—George R. Evanisko
(74) *Attorney, Agent, or Firm*—Schwegman, Lundberg, Woessner & Kluth, P.A.

(57) ABSTRACT

A telemetry system enabling radio-frequency communications between an implantable medical device and an external device which requires minimal power consumption by the implantable device. The implantable device uses an antenna tuning circuit to vary the impedance of an antenna and phase modulate a carrier signal reflected back to the external device with digital message data.

24 Claims, 3 Drawing Sheets

PASSIVE TELEMETRY SYSTEM FOR IMPLANTABLE MEDICAL DEVICE

FIELD OF THE INVENTION

This invention pertains to implantable medical devices such as cardiac pacemakers and implantable cardioverter/defibrillators. In particular, the invention relates to a telemetry system and method for such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Telemetry systems for implantable medical devices utilize radio-frequency (RF) energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand that can be positioned in proximity to the implanted device. The implantable device also generates and receives radio signals by means of an antenna, typically formed by a wire coil wrapped around the periphery of the inside of the device casing.

Most conventional radio-frequency telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. This requirement is an inconvenience for a clinician and limits the situations in which telemetry can take place.

Wireless radio-frequency communication over greater distances requires the use of far-field telemetry. Communication using far-field radiation can take place over much greater distances which makes it more convenient to use an external programmer. Also, the increased communication range makes possible other applications of the telemetry system such as remote monitoring of patients and communication with other types of external devices.

In order for a substantial portion of the energy delivered to an antenna to be emitted as far-field radiation, the wavelength of the driving signal should not be very much larger than the length of the antenna. Far-field radio-frequency communications with an antenna of a size suitable for use in an implantable device therefore requires a carrier in the frequency range of between a few hundred MHz to a few GHz. An active transmitter for this frequency range requires special RF components (typically including SiGe or GaAs semiconductor devices) that consume a significant amount of power (typically tens of milliwatts). There is no problem with providing such a transmitter in an external programmer which is connected to an external power source. Implantable medical devices, however, are powered by a battery contained within the housing of the device that can only supply a limited amount of peak power, and many batteries in use today are not capable of supplying power sufficient to power an RF transmitter. Even if sufficient power can be supplied, the battery has a limited life span. When the battery fails, it must be replaced which necessitates a reimplantation procedure. Implantable medical devices are also necessarily small, with only a limited space available for locating complex RF circuitry, especially in view of the fact that the RF circuitry needs to be isolated and shielded from the rest of the device circuitry to prevent interference. These factors make it difficult to satisfactorily implement a far-field RF transmitter in an implantable medical device.

SUMMARY OF THE INVENTION

The present invention is a telemetry system and method that enables far-field radio-frequency data transmission from an implantable medical device to an external device without the need for an active transmitter. In accordance with the invention, a radio-frequency carrier signal is transmitted from an antenna of the external device to an antenna of the implantable device. The impedance of the implantable device antenna is adjusted in a time varying manner with a tuning circuit in accordance with digital message data that is to be transmitted. The result is a phase modulated carrier signal reflected from the implantable device antenna back to the external device. The phase modulated carrier signal can then be demodulated at the external device to recover the digital message data.

DETAILED DESCRIPTION

Figure 1:
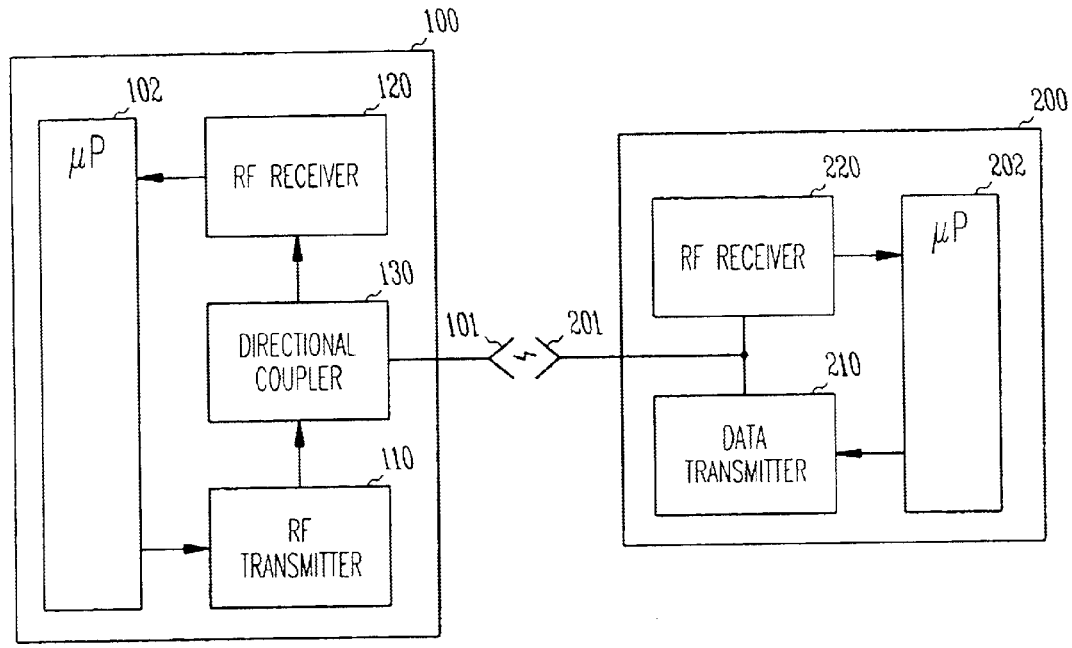
FIG. 1 illustrates the basic components of a passive telemetry system.

The present invention is a system and method for providing RF telemetry between an implantable medical device and an external device in which data is passively transmitted from the implantable device. The system allows far-field RF telemetry to be implemented without the need for an active transmitter in the implantable device FIG. 1 shows the primary telemetry components of an external device 100 and an implantable medical device 200. In this exemplary embodiment, the external device and the implantable device are microprocessor-based devices having microprocessors 102 and 202, respectively, that serve as controllers for overall device operation as well as supervising telemetry. The implantable device 200 may be a cardiac rhythm management device such as a pacemaker or implantable cardioverter/defibrillator, while the external device is a data-gathering device such as an external programmer or remote monitor.

The microprocessor 102 of the external device is interfaced to a radio-frequency transmitter 110 and receiver 120 that are both connected to an antenna 101. A directional coupler 130 passes radio-frequency signals unidirectionally from the transmitter to the antenna and from the antenna to the receiver. Upon a command from the microprocessor, the transmitter 110 generates a radio-frequency carrier signal for a specified time period that is emitted from the antenna 101. The transmitted carrier signal then reaches the antenna 201 of the implantable device where it is reflected back to the antenna 101 of the external device. By varying the impedance of the antenna 201, the implantable device modulates the phase of the reflected carrier in accordance with digital message data that is to be transmitted to the external device. After reaching the antenna 101, the reflected carrier signal is conveyed through the directional coupler to the receiver 120 where the signal is demodulated to extract the digital message data. The digital data may then be processed and interpreted by software executed by the microprocessor 102.

The directional coupler 130 of the external device enables the receiver 120 to receive signals without interference from signals simultaneously emitted by the antenna 101 that originate from the transmitter 110. As an alternative to the directional coupler, separate antennas with orthogonal linear polarization states can be provided for the transmitter and receiver, with the antenna of the implantable device then designed to reflect elliptically polarized radio waves. For example, the antennas of the external device transmitter and receiver may be monopole or dipole antennas oriented at right angles to one another, while the implantable device antenna is a loop or helical antenna. The external device receiver antenna is blind to waves radiated by the transmitter antenna but is sensitive to waves reflected by the implantable device antenna, thus enabling simultaneous radiation of the carrier signal by the transmitter antenna and reception of the reflected carrier by the receiver antenna. Another alternative to using a directional coupler is for the external device to transmit the carrier signal in discrete bursts and receive the signal reflected by the implantable device between the bursts, with the transmitter and receiver being alternately connected to the antenna by a switch.

In the implantable device 200, the microprocessor is interfaced to a data transmitter 210 that includes circuitry for encoding digital message data received from the microprocessor and time-varying the impedance of the antenna 201 accordingly. A radio-frequency carrier signal reflected from the antenna while the impedance is so varied is thus phase modulated with the digital data using some variant of phase-shift keying. In one embodiment, the implantable device periodically varies the antenna impedance with the same message data in order to transmit the data whenever an external device transmits a carrier signal. In another embodiment, a radio-frequency receiver 220 is provided as shown in the figure that enables the external device to communicate with the implantable device. Such radio-frequency communications may take place over a different communications channel using a different carrier frequency and/or modulation method than used in the passive telemetry system described herein. When the implantable device receives a data request from the external device, it may then expect the carrier signal to be transmitted and can initiate a data transfer by varying the impedance of the antenna. Although a radio-frequency receiver does consume a significant amount of power, this is minimized by only using it for short periods in order to initiate communications with passive telemetry.

Figure 2:
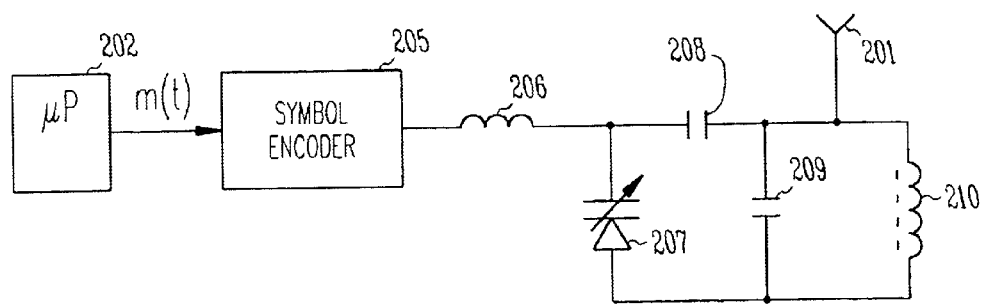
FIG. 2 is a diagram of a data transmitter for the implantable device.

FIG. 2 shows an exemplary implementation of the data transmitter 210 of the implantable device. Digital message data m(t) is passed to a symbol encoder 205 that includes a digital-to-analog converter for encoding the digital data into voltage level symbols that are output serially at a specified symbol rate and used to vary the impedance of the antenna 201 via a tuning circuit. For example, binary symbols are generated by outputting one voltage level for each 1 in the message data m(t) and another voltage level for each 0. The tuning circuit is connected to the antenna 201 and thus constitutes part of the impedance presented to a carrier signal reflected by the antenna. In this embodiment, the tuning circuit is an LC tank circuit with a voltage-controlled capacitance. As shown in the figure, the tank circuit includes an inductor 210, a capacitor 209, and a varactor diode 207. The voltage level symbols output by the symbol encoder 205 are applied across the varactor diode 207 and thereby vary the capacitance of the tank circuit in accordance therewith. Since the phase of a waveform reflected by the antenna depends upon the complex impedance of the tank circuit, the voltage level symbols are thus converted to phase angle symbols in the reflected carrier signal. The symbol rate is normally specified such that the symbol period $T_S$ is some number of cycles of the carrier signal. Also shown in the figure is a choke inductor 206 for isolating the symbol encoder from radio-frequency signals and a DC blocking capacitor 208 that isolates the antenna from the voltage applied to the varactor diode.

Figure 3:
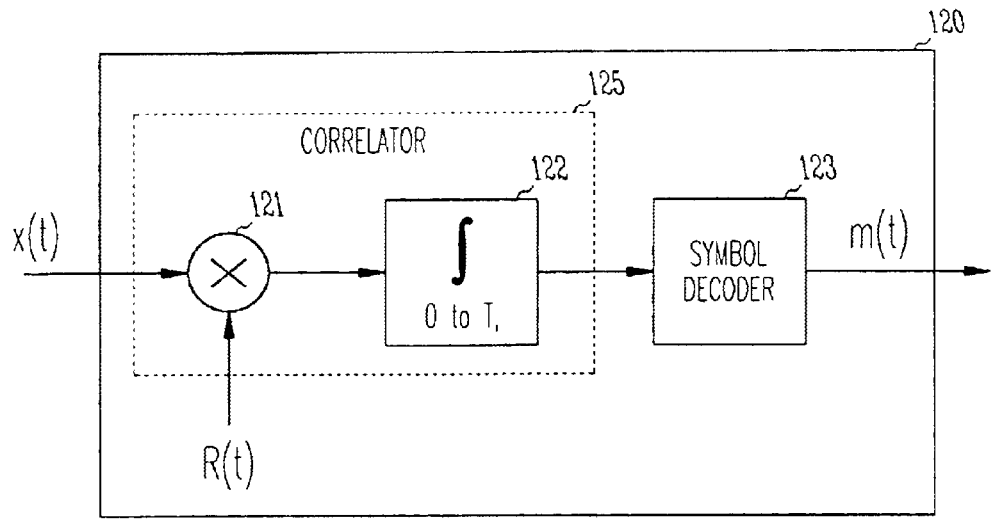
FIG. 3 is a block diagram of an external device receiver for binary phase-shift keying.
Figure 4:
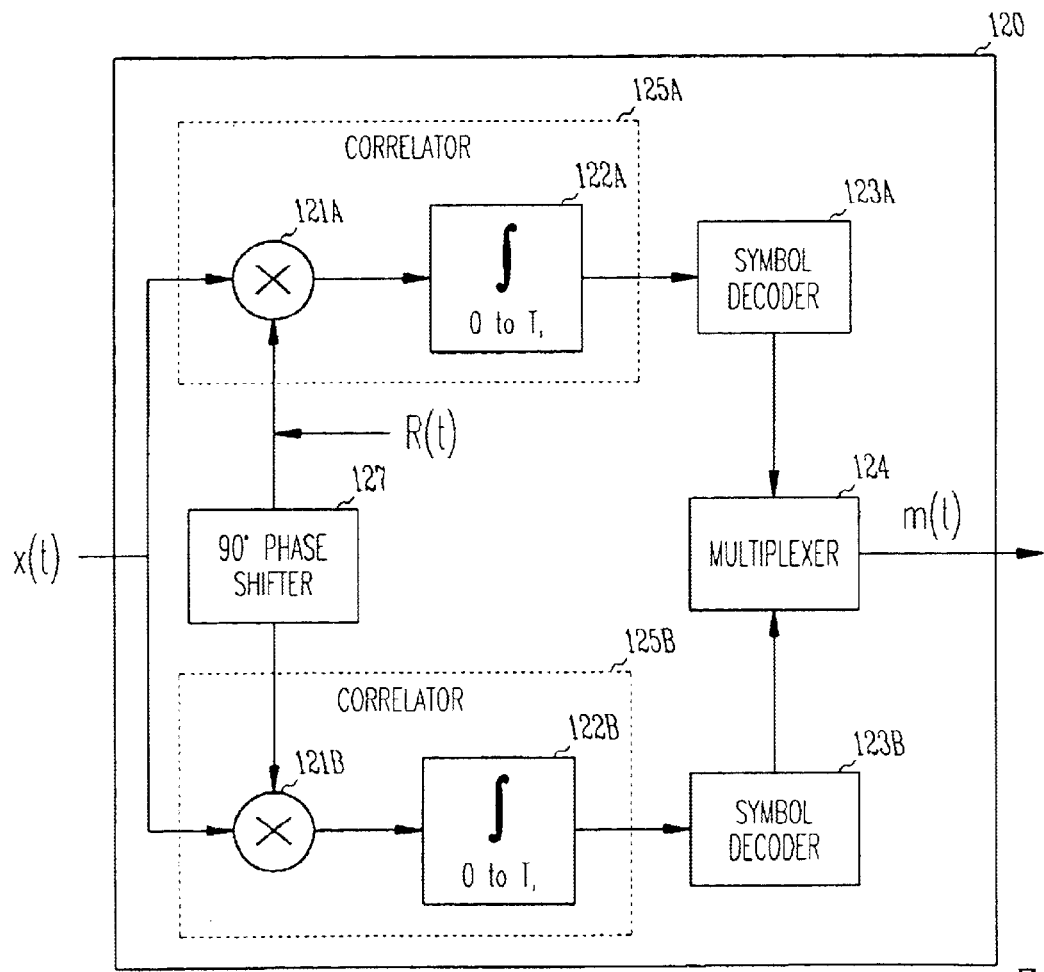
FIG. 4 is a block diagram of an external device receiver for quadrature phase-shift keying.

FIG. 3 shows an exemplary implementation of an external device receiver 120 for demodulating a radio-frequency carrier reflected from the implantable device. In this example, the reflected carrier x(t) is modulated with digital message data m(t) by the implantable device using binary phase-shift keying and then synchronously demodulated at the external device. In conventional binary phase-shift keying, the phase of the carrier is either shifted 180 degrees or not in accordance with the modulating digital data. In synchronous demodulation, a reference carrier signal is used to detect the phase of the received signal. A correlator 125, made up of mixer 121 and integrator 122, correlates the received signal x(t) with a reference carrier signal R(t) over a symbol period $T_S$ in order to convert the phase angle symbols contained in x(t) into voltage level symbols. The voltage level symbols are then decoded by symbol decoder 123 to result in the extracted message data m(t). FIG. 4 shows another example of a receiver 120 in which the reflected carrier x(t) is modulated with message data using quadrature phase-shift keying where two bits of digital data are represented by one of four phase angle symbols, normally spaced 90 degrees apart. In this case, the signal x(t) is correlated with a reference signal R(t) over the symbol period $T_S$ by correlator 125a in order to demodulate the in-phase component of the signal x(t). The quadrature component of the signal x(t) is demodulated by correlator 125b which correlates x(t) with the reference signal R(t) shifted by 90 degrees, the latter being generated by phase shifter 127. Symbol decoders 123a and 123b then convert the voltage level symbols output by correlators 125a and 125b, respectively, into binary digital data which are input to multiplexer 124 to generate the extracted message data m(t). Other embodiments may use M-ary phase-shift keying where additional phase angle symbols are used to represent greater numbers of bits. The upper limit on the amount of information that can be packed into a symbol is determined by the signal-to-noise ratio of the communications channel.

In one embodiment, the reference carrier R(t) used in the examples of FIGS. 3 and 4 may be a locally generated signal using the same oscillator used to generate the carrier signal emitted by the antenna 101. In that case, the phase of the reference signal R(t) must match the phase of the unmodulated carrier received from the implantable device in order to demodulate the received signal. Since the phase of the received signal x(t) varies with the distance between the implantable device and the external device, the implantable device may, at specified times according to a predetermined communications protocol, reflect radio-frequency carrier signal with alignment or reference symbols having no phase shift with which the external device receiver may synchronize the reference carrier signal.

The external device may transmit the carrier signal to the implantable device in bursts having durations of one symbol period or a plurality of symbol periods. In the former case, the phase shift of each reflected burst is detected in order to determine which symbol is being transmitted. A burst with a reference symbol (i.e., with zero phase shift) is periodically reflected by the implantable device so that the phase of reference carrier can be adjusted, and succeeding bursts are then transmitted at regular intervals in order to maintain the proper phase relationship between the reference carrier and the reflected carrier. In an exemplary implementation, a 403 MHz carrier is employed for data transmission, as the FCC has recently set aside a nominal frequency of 403 MHz channelized into 300 kHz channels for medical device communications. In order to constrain the data transmission to a bandwidth of less than 300 kHz, 10 microsecond bursts of the carrier are transmitted, with each burst separated by an interval of 10 microseconds. With one symbol per burst, the symbol rate is then 50 kilosymbols per second, which is well below the theoretical maximum of 600 kilosymbols per second allowed by the 300 kHz channel. If the data is encoded as two bits per symbol (i.e., quadrature phase-shift keying), the maximum data rate attainable by this particular scheme is then 100 kilobits per second, minus the overhead associated with periodically transmitting reference symbols.

Figure 5A:
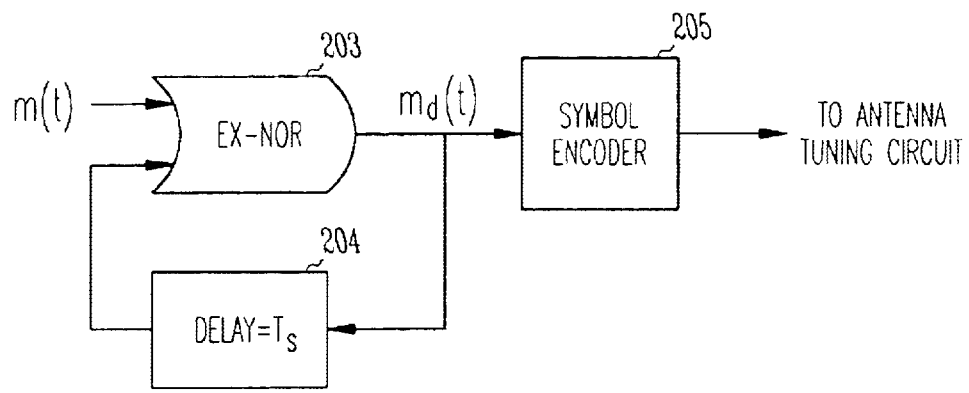
FIG. 5A is an exemplary circuit for differential data encoding.
Figure 5B:
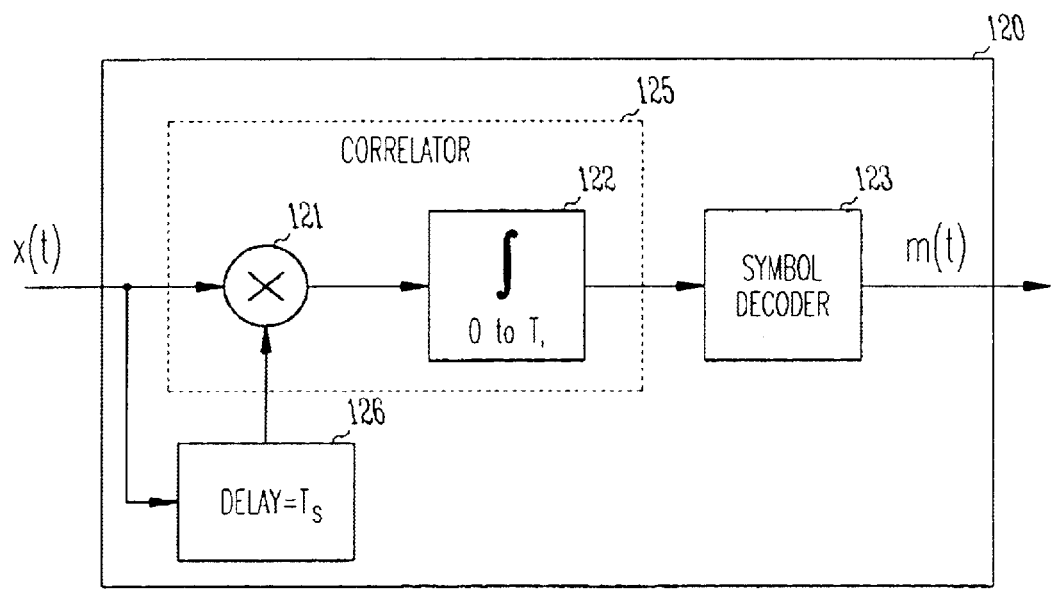
FIG. 5B is a block diagram of an external device receiver for differential binary phase-shift keying.

In another embodiment, each burst of the carrier signal transmitted by the external device is modulated with a plurality of symbols by the reflecting antenna of the implantable device. The duration of the bursts may then be made arbitrarily long so that data transmission is continuous while the external device is transmitting. Each reflected burst may then contain one or more reference symbols in order to maintain the locally generated reference carrier at the proper phase. As an alternative to employing a reference carrier to demodulate the reflected signal, the data may be transmitted by the implantable device using differential phase-shift keying. In this type of modulation, symbols are encoded into the carrier waveform as the phase shifts between succeeding symbol periods rather than with respect to a reference carrier. This allows demodulation to be accomplished without the need for generating a reference carrier. FIG. 5A shows an example circuit by which the implantable device may differentially encode digital message data m(t) received from the microprocessor 202. The data signal m(t) is fed to one of the inputs of exclusive-NOR gate 203, with the other input being the output of the gate delayed by one bit period $T_B$. The one-bit delay can be implemented by a clocked shift-register. The resulting data signal $m_d(t)$ contains the data of m(t) encoded such that a logical 1 is represented by a change of logic state from the previous bit, and a logical 0 is represented by no change in logic state from the previous bit. The data signal $m_d(t)$ is then used by the symbol encoder 205 to vary the impedance of the antenna as described above. The reflected carrier signal is thus modulated with differential phase-shift keying and can be demodulated by the receiver 120 of the external device with the exemplary implementation shown in FIG. 5B. There, the correlator 125, made up of mixer 121 and integrator 122, correlates the signal x(t) with the same signal delayed by one symbol period $T_S$, the delay being implemented by delay element 126. The correlation is performed over the symbol period $T_S$ such that each symbol of the received carrier signal x(t) is correlated with the previous symbol in x(t) which simultaneously demodulates the carrier and differentially decodes the message data signal $m_d(t)$. The output of the correlator is then converted to digital data by symbol decoder 123 to recover the message data signal m(t).

It should be appreciated that the demodulation of the carrier signal by the external device in any of the embodiments described above may be accomplished by either analog circuit elements or entirely in the digital domain. In the latter case, the reflected carrier signal is received by the antenna of the external device and digitized using a sampling rate at least twice that of the carrier frequency. The correlation operations may then be performed by code executed by the microprocessor or a dedicated digital signal processor.

A complicating factor in implementing a passive telemetry system that has not been mentioned thus far is the backscattering of the carrier signal by surfaces other than the antenna of the implantable device. When the carrier signal is transmitted to the implantable device by the external device, the signal is reflected by other surfaces in the environment and received by the external device antenna at various phase angles in addition to the modulated carrier signal. Even if a reference carrier is properly generated or differential phase-shift keying is used, the additive effects of this backscattered radiation decreases the phase distance between the symbols of the modulated carrier. For example, the 0 and 180 degree phase shifts used to represent symbols in binary phase-shift keying may be received by the external device as 0 and 20 degrees of phase shift. In order to compensate for this effect, the voltage thresholds used by the symbol decoder 123 to convert the output of the correlator 125 into digital data need to be adjusted accordingly so that the actual phase shifts detected by the correlator are interpreted as symbols. Such adjustments of the symbol thresholds may be made manually or dynamically using a training sequence.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A telemetry system for enabling transfer of message data from an implantable medical device to an external device, comprising:

an implantable medical device;

an external device;

a transmitter and a transmitter antenna incorporated as part of the external device for transmitting a radio-frequency carrier signal to the implantable device;

an implantable device antenna incorporated as part of the implantable device for reflecting the radio-frequency carrier signal;

a tuning circuit incorporated as part of the implantable device for adjusting the impedance of the implantable device antenna in a time varying manner so as to phase modulate the radio-frequency carrier signal reflected therefrom in accordance with the message data;

a receiver and a receiver antenna incorporated as part of the external device for receiving the phase modulated carrier signal reflected from the antenna of the implantable device and extracting the message data therefrom; and, wherein the transmitter and receiver antennas are linearly polarizing antennas orthogonal to one another and the implantable device antenna is elliptically polarizing.

2. The system of claim 1 wherein the frequency of the radio-frequency carrier signal and the dimensions of the antennas are such that a significant portion of the radio-frequency energy emitted by the external device antenna and reflected by the implantable device antenna is far-field radiation.

3. The system of claim 1 further comprising a receiver incorporated as part of the implantable device for receiving a radio-frequency carrier modulated with digital data from the external device.

4. The system of claim 1 wherein the tuning circuit comprises a symbol encoder for encoding the message data into corresponding voltage level symbols that are used to adjust the impedance of the implantable device antenna in a time varying manner so that the radio-frequency carrier signal is reflected with a phase-shift corresponding to each symbol.

5. The system of claim 4 wherein the antenna tuning circuit further comprises a tank circuit with a voltage-controlled capacitance adjusted by the symbol encoder in accordance with the message data.

6. The system of claim 5 wherein the voltage-controlled capacitance is a varactor diode.

7. The system of claim 4 wherein the message data is encoded into binary symbols by the symbol encoder such that the reflected radio-frequency carrier is modulated with binary phase-shift keying.

8. The system of claim 4 wherein the message data is encoded into four symbols by the symbol encoder such that the reflected radio-frequency carrier is modulated with quadrature phase-shift keying.

9. The system of claim 4 wherein the external device receiver comprises a demodulator and a symbol decoder for recovering the message data from the reflected radio-frequency carrier signal.

10. The system of claim 9 wherein the demodulator is a synchronous demodulator.

11. The system of claim 10 wherein the external device generates a reference carrier signal that is correlated with the reflected radio-frequency signal by the synchronous demodulator.

12. The system of claim 11 wherein the implantable device, at specified times according to a predetermined communications protocol, is adapted to modulate the reflected radio-frequency carrier signal with no phase shift in order to generate alignment symbols for use by the external device receiver in synchronizing the reference carrier signal to the reflected carrier signal.

13. The system of claim 9 wherein the symbol encoder differentially encodes the message data such that symbols are represented in the modulated carrier by the phase change from one symbol period to another.

14. The system of claim 13 wherein the demodulator of the external device receiver is adapted to correlate the radio-frequency signal reflected from the implantable device with the same signal delayed by a symbol period.

15. The system of claim 14 wherein the tuning circuit is adapted to modulate the radio-frequency carrier reflected from the implantable device with differential binary phase-shift keying.

16. The system of claim 14 wherein the tuning circuit is adapted to modulate the radio-frequency carrier reflected from the implantable device with differential quadrature phase-shift keying.

17. A method for enabling data transfer from an implantable medical device to an external device, comprising:

transmitting a radio-frequency carrier signal from a transmitter antenna of the external device to an antenna of the implantable device which reflects the radio-frequency carrier signal;

adjusting the impedance of the implantable device antenna in a time varying manner so as to phase modulate the radio-frequency carrier signal reflected therefrom in accordance with a digital data signal; and, receiving the phase modulated carrier signal reflected from the implantable device antenna at a receiver antenna of the external device and extracting the digital data signal therefrom;

wherein the transmitter and receiver antennas are linearly polarizing antennas orthogonal to one another and the implantable antenna is elliptically polarizing.

18. The method of claim 17 further comprising transmitting the radio-frequency carrier signal at a frequency such that a significant portion of the radio-frequency energy emitted by the external device antenna and reflected by the implantable device antenna is far-field radiation.

19. The method of claim 17 further comprising encoding the digital data signal into corresponding voltage level symbols and adjusting the impedance of the implantable device antenna for a specified symbol period so that the radio-frequency carrier is reflected with a phase-shift corresponding to each symbol.

20. The method of claim 19 wherein the impedance of the implantable device antenna is adjusted by adjusting a voltage-controlled capacitance of a tank circuit connected to the antenna.

21. The method of claim 17 further comprising synchronously demodulating the signal received at the external device by correlating the signal reflected from the implantable device with a locally generated reference carrier signal.

22. The method of claim 21 further comprising periodically modulating the reflected radio-frequency carrier signal with alignment symbols having no phase shift in order for the external device receiver to generate a synchronized reference carrier signal.

23. The method of claim 17 further comprising differentially encoding the digital data at the implantable device such that symbols are represented in the modulated carrier by the phase change from one symbol period to another.

24. The method of claim 23 further comprising demodulating the signal received at the external device by correlating the signal reflected from the implantable device with the same signal delayed by a symbol period.

* * * * *

UNITED STATES PATENT AND TRADEMARK OFFICE
CERTIFICATE OF CORRECTION

| | |
|---|---|
| PATENT NO. | : 6,889,086 B2 |
| APPLICATION NO. | : 09/828460 |
| DATED | : May 3, 2005 |
| INVENTOR(S) | : Mass et al. |

It is certified that error appears in the above-identified patent and that said Letters Patent is hereby corrected as shown below:

On the Title page, in Item [56], under "U.S. Patent Documents", in column 2, line 3, after "Silvian" insert -- 607/59 --.

Signed and Sealed this

Fifth Day of December, 2006

JON W. DUDAS
*Director of the United States Patent and Trademark Office*